Figure 1:
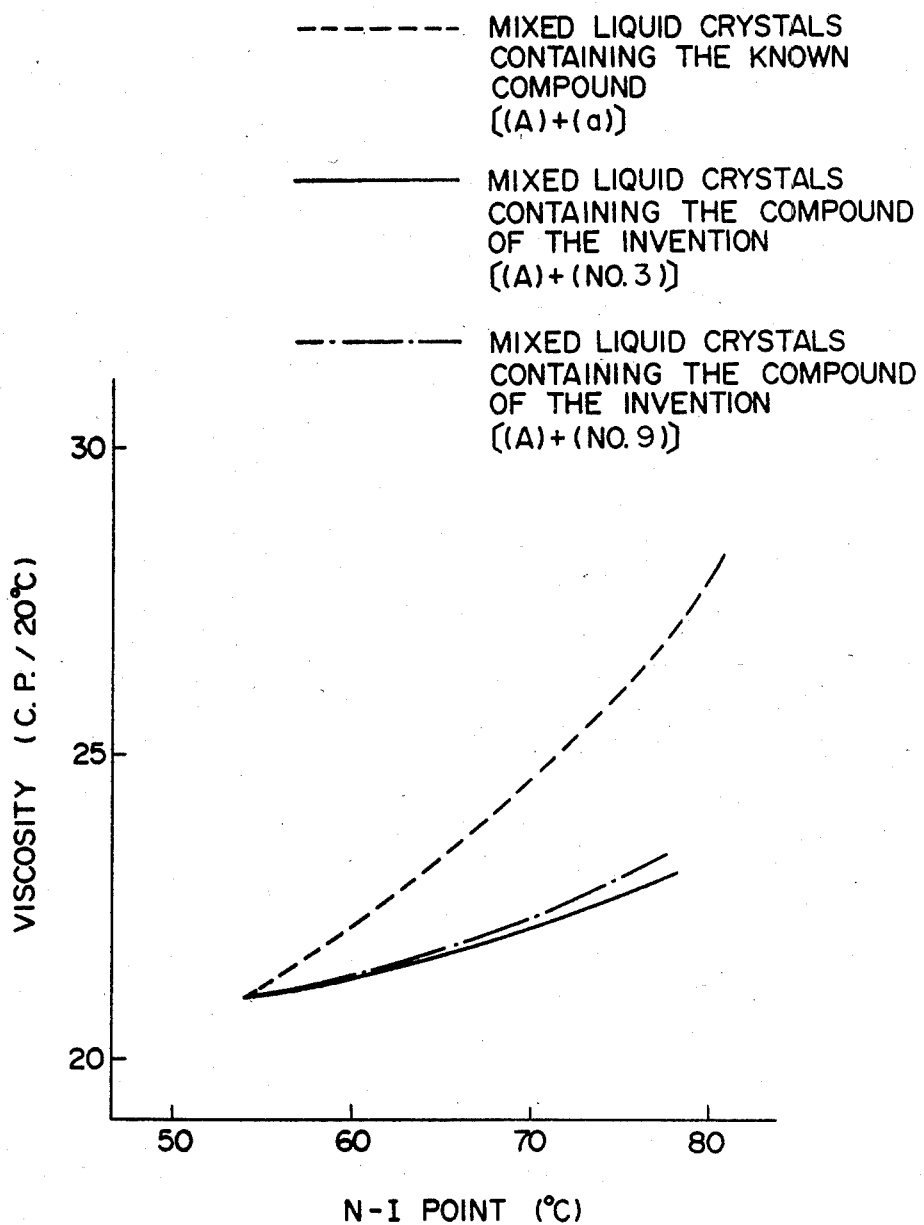

United States Patent [19]

Takatsu et al.

[11] Patent Number: 4,558,151
[45] Date of Patent: Dec. 10, 1985

[54] NEMATIC LIQUID CRYSTALLINE COMPOUNDS

[75] Inventors: Haruyoshi Takatsu, Kodaira; Hisato Sato, Tokyo, both of Japan

[73] Assignee: Dainippon Ink and Chemicals, Inc., Tokyo, Japan

[21] Appl. No.: 546,511

[22] Filed: Oct. 28, 1983

[30] Foreign Application Priority Data

| Oct. 30, 1982 | [JP] | Japan | 57-191064 |
| Dec. 17, 1982 | [JP] | Japan | 57-221196 |
| Dec. 17, 1982 | [JP] | Japan | 57-221197 |
| Mar. 18, 1983 | [JP] | Japan | 58-44331 |

[51] Int. Cl.$^4$ .................. C09K 3/34; C07C 69/753; G02F 1/13
[52] U.S. Cl. .................. 560/118; 252/299.63; 350/350 R; 350/350 S
[58] Field of Search ........... 252/299.63; 350/350 R, 350/350 S; 560/118

[56] References Cited

U.S. PATENT DOCUMENTS

| 4,229,315 | 10/1980 | Krause et al. | 252/299.63 |
| 4,340,498 | 7/1982 | Sugimori et al. | 252/299.5 |
| 4,349,452 | 9/1982 | Osman et al. | 252/299.63 |
| 4,361,494 | 11/1982 | Osman et al. | 252/299.63 |
| 4,387,039 | 6/1983 | Sugimori et al. | 252/299.63 |
| 4,393,258 | 7/1983 | Sato et al. | 252/299.63 |
| 4,399,298 | 8/1983 | Sugimori et al. | 252/299.63 |
| 4,400,293 | 8/1983 | Romer et al. | 252/299.63 |
| 4,419,263 | 12/1983 | Praefcke et al. | 252/299.63 |
| 4,439,015 | 3/1984 | Rich et al. | 252/299.63 |
| 4,455,443 | 6/1984 | Takatsu et al. | 252/299.5 |
| 4,460,770 | 7/1984 | Petrzilka et al. | 252/299.63 |
| 4,472,592 | 9/1984 | Takatsu et al. | 252/299.63 |
| 4,473,487 | 9/1984 | Romer et al. | 252/299.65 |
| 4,480,117 | 10/1984 | Takatsu et al. | 252/299.63 |
| 4,487,954 | 12/1984 | Sugimori et al. | 252/299.63 |
| 4,514,044 | 4/1985 | Gunjima et al. | 252/299.63 |

FOREIGN PATENT DOCUMENTS

| 56501 | 7/1982 | European Pat. Off. | 252/299.61 |
| 58512 | 8/1982 | European Pat. Off. | 252/299.63 |
| 87102 | 8/1983 | European Pat. Off. | 252/299.63 |
| 87032 | 8/1983 | European Pat. Off. | 252/299.63 |
| 103681 | 3/1984 | European Pat. Off. | 252/299.63 |
| 3237367 | 4/1983 | Fed. Rep. of Germany | 252/299.63 |
| 3211601 | 10/1983 | Fed. Rep. of Germany | 252/299.63 |
| 3324774 | 1/1984 | Fed. Rep. of Germany | 252/299.63 |
| 3318533 | 1/1984 | Fed. Rep. of Germany | 252/299.63 |
| 3335550 | 4/1984 | Fed. Rep. of Germany | 252/299.63 |
| 57-4645 | 4/1982 | Japan | 252/299.63 |
| 57-91953 | 6/1982 | Japan | 252/299.63 |
| 58-8022 | 1/1983 | Japan | 252/299.63 |
| 58-65251 | 4/1983 | Japan | 252/299.63 |

OTHER PUBLICATIONS

Anon., Res. Discl., vol. 241, p. 194 (1984).

*Primary Examiner*—Teddy S. Gron
*Attorney, Agent, or Firm*—Sherman & Shalloway

[57] ABSTRACT

A compound represented by the general formula

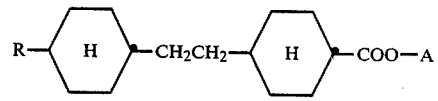

wherein A denotes

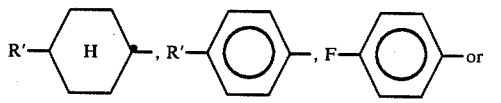

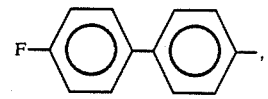

R and R', independently from each other, denote a linear alkyl group having 1 to 9 carbon atoms, and (Abstract continued on next page.)

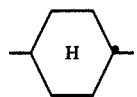 is a cyclohexane ring arranged in a trans(equatorial-equatorial)form.
2 Claims, 2 Drawing Figures

NEMATIC LIQUID CRYSTALLINE COMPOUNDS

This invention relates to novel nematic liquid crystalline compounds useful as electro-optical display materials.

The novel nematic liquid crystalline compounds provided by this invention are compounds of the general formula

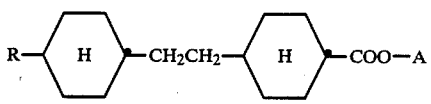

wherein A denotes

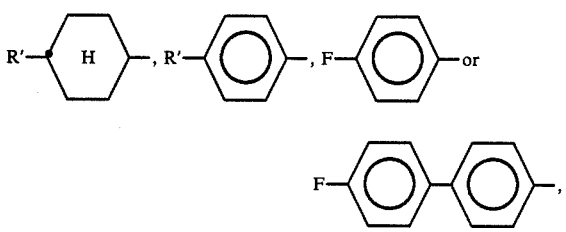

R and R', independently from each other, denote a linear alkyl group having 1 to 9 carbon atoms, and

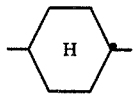

is a cylohexane ring arranged in a trans(equatorial-equatorial)form.

Typical liquid crystal display cells include, for example, a field effect mode cell proposed by M. Schadt et al. [Applied Physics Letters, 18, 127–128 (1971)], a dynamic scattering mode cell proposed by G. H. Heilmeier [Proceedings of the I.E.E.E., 56, 1162–1171 (1968)], and a guest-host mode cell proposed by G. H. Heilmeier [Applied Physics Letters, 13, 91 (1968)] or D. L. White, et al. [Journal of Applied Physics, 45, 4718 (1974)].

Liquid crystalline materials used in these liquid crystal display cells are required to have various properties. An important property required commonly of various display cells is that the liquid crystalline materials have a nematic phase over a broad temperature range including room temperature. Many practical materials having such property are usually prepared by mixing at least one compound having a nematic phase near room temperature with at least one compound having a nematic phase at temperatures higher than room temperature. Many of mixed liquid crystals of the above type now in practical use are required to have a nematic phase at least over an entire temperature range of from −30° C. to +65° C. In order to meet such requirement, compounds having a crystalline nematic phase transition temperature (C-N) point of about 100° C. and a nematic-isotropic liquid phase transition temperature (N-I) point of about 200° C., such as 4,4'-substituted terphenyl, 4,4'-substituted biphenylcyclohexane and phenyl 4,4' -substituted benzoyloxybenzoate are used in many cases as compounds having a nematic phase in the range of temperatures higher than room temperature. However, these compounds, when mixed in amounts sufficient to make the N-I point of mixed liquid crystals at least 65° C., increase the viscosity of the resulting mixed liquid crystals, which undesirously decreases the speed of response.

The compounds of the formula (I) in accordance with this invention are novel compounds with properties improved. That is, when the compounds of the formula (I) are mixed with one or more of other nematic liquid crystalline compounds to prepare practical mixed liquid crystals having the N-I point of at least 65° C., said compounds can increase the viscosity of mixed liquid crystals to a far lesser extent than the known liquid crystalline compounds. Moreover, the compounds of formula (I) have very good compatibility with phenyl 4,4'-substituted cyclohexylcarboxylates which are reported in the specification of U.S. Pat. No. 4,372,871 as nematic liquid crystalline materials having excellent characteristics for time multiplex drive. Therefore, better mixed liquid crystals can be obtained by mixing the compounds of formula (I) with these compounds.

The compounds of formula (I) in accordance with this invention can be produced in the following process.

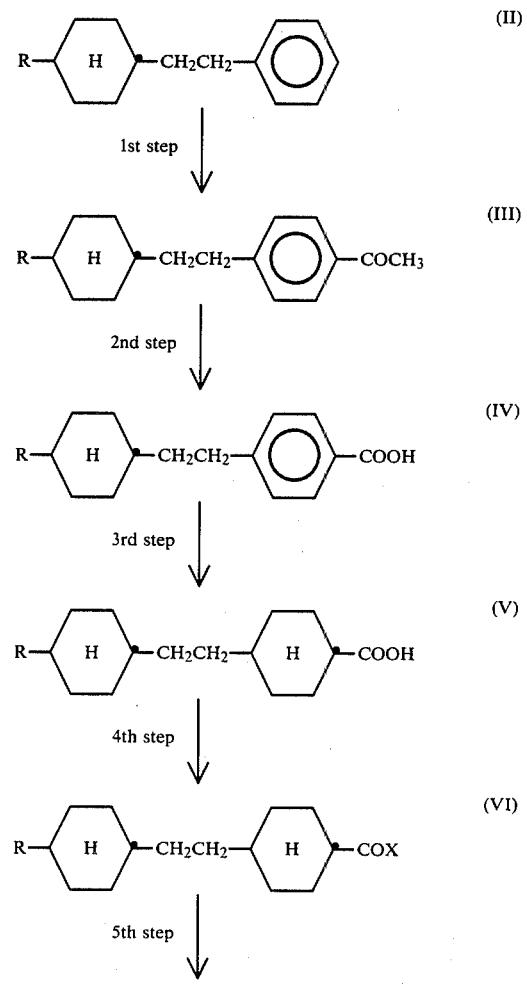

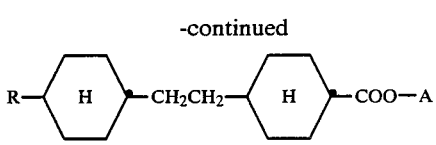

wherein R and A are as defined above and X denotes a halogen atom.

1st Step

The compound of the formula (II) is reacted with acetyl chloride and anhydrous aluminum chloride in carbon disulfide and nitrobenzene to form the compound of the formula (III).

2nd Step

The compound of the formula (III) is reacted with a sodium hydroxide solution of sodium hypochlorite or sodium hypobromite in dioxane to provide the compound of the formula (IV).

3rd Step

The compound of the formula (IV) is hydrogenated with a reduction catalyst such as Ru—C, etc. in a sodium hydroxide solution. Said compound is then acidified and a free carboxylic acid is taken out and thermally transformed. Thus, the compound of the formula (V) results.

4th Step

The compound of the formula (V) is reacted with a halogenating agent to afford the compound or the formula (VI). In the compound of the formula (VI), X is preferably a chlorine atom. Thionyl chloride is preferable as a halogenating agent.

5th Step

The compound of the formula (VI) formed in the 4th step is reacted with a compound of the formula A—OH in an inert organic solvent such as ether, benzene, toluene, etc. using as a catalyst a basic compound such as pyridine to afford the compound of the formula (I) in accordance with this invention.

The typical compounds of the formula (I) thus formed have transition temperatures shown in Table 1.

TABLE 1

R—[H]—CH$_2$CH$_2$—[H]—COO—A

| No. | R | A | Transition temperatures (°C.) | | |
|---|---|---|---|---|---|
| 1 | C$_2$H$_5$— | n-C$_3$H$_7$—[H]— | 142(C→N) | | 155(N⇌I) |
| 2 | n-C$_3$H$_7$— | C$_2$H$_5$—[H]— | 140(C→N) | | 151(N⇌I) |
| 3 | n-C$_3$H$_7$— | n-C$_3$H$_7$—[H]— | 153(C→N) | | 166(N⇌I) |
| 4 | n-C$_3$H$_7$— | n-C$_5$H$_{11}$—[H]— | 157(C→N) | | 169(N⇌I) |
| 5 | n-C$_5$H$_{11}$— | n-C$_3$H$_7$—[H]— | 154(C→N) | | 167(N⇌I) |
| 6 | n-C$_5$H$_{11}$— | n-C$_5$H$_{11}$—[H]— | 146(C→S) | 155 (S⇌N) | 161(N⇌I) |
| 7 | C$_2$H$_5$— | n-C$_3$H$_7$—[phenyl]— | 115(C→N) | | 152(N⇌I) |

TABLE 1-continued

R—[H]—CH₂CH₂—[H]—COO—A

| No. | R | A | Transition temperatures (°C.) | | |
|---|---|---|---|---|---|
| 8 | n-C₃H₇— | C₂H₅—⟨◯⟩— | 112(C→N) | | 149(N⇌I) |
| 9 | n-C₃H₇— | n-C₃H₇—⟨◯⟩— | 128(C→S) | 131(S⇌N) | 165(N⇌I) |
| 10 | n-C₃H₇— | n-C₅H₁₁—⟨◯⟩— | 129(C→S) | 135(S⇌N) | 167(N⇌I) |
| 11 | n-C₅H₁₁— | n-C₃H₇—⟨◯⟩— | 127(C→S) | 134(S⇌N) | 166(N⇌I) |
| 12 | n-C₅H₁₁— | n-C₅H₁₁—⟨◯⟩— | 124(C→S) | 147(S⇌N) | 163(N⇌I) |
| 13 | C₂H₅— | F—⟨◯⟩— | 70(C→N) | | 136(N⇌I) |
| 14 | n-C₃H₇— | F—⟨◯⟩— | 81(C→N) | | 156(N⇌I) |
| 15 | n-C₄H₉— | F—⟨◯⟩— | 67(C→N) | | 148(N⇌I) |
| 16 | n-C₅H₁₁— | F—⟨◯⟩— | 83(C→N) | | 152(N⇌I) |
| 17 | C₂H₅— | F—⟨◯⟩—⟨◯⟩— | 145(C→N) | | 248(N⇌I) |
| 18 | n-C₃H₇— | F—⟨◯⟩—⟨◯⟩— | 159(C→N) | | 260(N⇌I) |
| 19 | n-C₄H₉— | F—⟨◯⟩—⟨◯⟩— | 142(C→N) | | 251(N⇌I) |

TABLE 1-continued

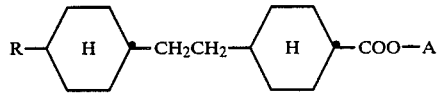

| No. | R | A | Transition temperatures (°C.) | |
|---|---|---|---|---|
| 20 | n-C$_5$H$_{11}$— |  | 164(C→N) | 258(N⇌I) |

NOTE:
In Table 1, C represents a crystalline phase; S, a smectic phase; N, a nematic phase; and I, an isotropic liquid phase. An arrow shows a phase transition.

The compounds of formula (I) in accordance with this invention are nematic liquid crystal compounds having a weak positive dielectric anisotropy and can therefore be used, for example, as materials for dynamic scattering mode cells in the form of mixtures with other nematic liquid crystalline compounds having a negative or weak positive dielectric anisotropy, or as materials for field effect mode display cells in the form of mixtures with other nematic liquid crystal compounds having a strong positive dielectric anisotropy.

Typical examples of the nematic liquid crystalline compounds which can preferably be used in admixture with the compounds of the formula (I) include phenyl 4,4'-substituted benzoates, phenyl 4,4'-substituted cyclohexanecarboxylates, biphenyl 4,4'-substituted cyclohexanecarboxylates, 4'-substituted phenyl 4(4-substituted cyclohexanecarbonyloxy)benzoates, 4'-substituted phenyl 4(4-substituted cyclohexyl)benzoates, 4'-substituted cyclohexyl 4(4-substituted cyclohexyl)benzoates, 4,4'-biphenyl, 4,4'-phenylcyclohexane, 4,4'-substituted terphenyl, 4,4'-biphenylcyclohexane, and 2(4'-substituted phenyl)-5-substituted pyrimidine.

Table 2 shows the N-I points and viscosities measured for mixed liquid crystals composed of 80% by weight of the matrix liquid crystals now in widespread use as nematic liquid crystalline materials having excellent characteristics for time multiplex drive and 20% by weight of the compounds Nos. 1 to 16 of the formula (I) shown in Table 1 as well as for mixed liquid crystals composed of 90% by weight of the matrix liquid crystals (A) and 10% by weight of the compounds Nos. 17 to 20 of the formula (I) shown in Table 1. The same table also indicates the N-I point and viscosity measured for the matrix liquid crystals (A) for comparison too.

The matrix liquid crystals (A) comprise

20% by weight of n-C$_3$H$_7$——CN,

16% by weight of n-C$_5$H$_{11}$——CN,

16% by weight of n-C$_7$H$_{15}$——CN,

8% by weight of n-C$_3$H$_7$——COO——OC$_2$H$_5$,

8% by weight of n-C$_3$H$_7$——COO——O—n-C$_4$H$_9$,

-continued

8% by weight of n-C$_4$H$_9$——COO——OCH$_3$,

8% by weight of n-C$_4$H$_9$——COO——OC$_2$H$_5$,

8% by weight of n-C$_5$H$_{11}$——COO——OCH$_2$ and

8% by weight of n-C$_5$H$_{11}$——COO——OC$_2$H$_5$.

TABLE 2

| | N-I point (°C.) | Viscosity (c.p./20° C.) |
|---|---|---|
| (A) | 54.0 | 21.0 |
| (A) + (No. 1) | 73.8 | 22.8 |
| (A) + (No. 2) | 73.0 | 22.8 |
| (A) + (No. 3) | 76.2 | 22.9 |
| (A) + (No. 4) | 76.6 | 23.1 |
| (A) + (No. 5) | 76.3 | 23.2 |
| (A) + (No. 6) | 75.0 | 23.4 |
| (A) + (No. 7) | 73.6 | 23.0 |
| (A) + (No. 8) | 72.9 | 23.0 |
| (A) + (No. 9) | 76.0 | 23.1 |
| (A) + (No. 10) | 76.3 | 23.3 |
| (A) + (No. 11) | 76.3 | 23.3 |
| (A) + (No. 12) | 75.1 | 23.6 |
| (A) + (No. 13) | 70.1 | 23.4 |
| (A) + (No. 14) | 74.0 | 23.5 |
| (A) + (No. 15) | 72.5 | 24.3 |
| (A) + (No. 16) | 73.2 | 24.1 |
| (A) + (No. 17) | 72.0 | 23.3 |
| (A) + (No. 18) | 73.2 | 23.4 |
| (A) + (No. 19) | 72.2 | 24.1 |
| (A) + (No. 20) | 72.9 | 24.0 |

From the data shown in Table 2, it can be understood that the compounds of formula (I) can thoroughly increase the N-I point of mixed liquid crystals to a practically sufficient extent without greatly increasing the viscosity thereof. The viscosity value of about 24 centipoises/20° C. is much lower than viscosities of various mixed liquid crystals which have the N-I point of at least 65° C. and are now on an average practical level. The high practical value of the compounds represented by the formula (I) lies in that they can give mixed liquid crystals having such low viscosities.

The superiority provided by the compounds of this invention is illustrated by the following Comparative Examples.

Figure 2:
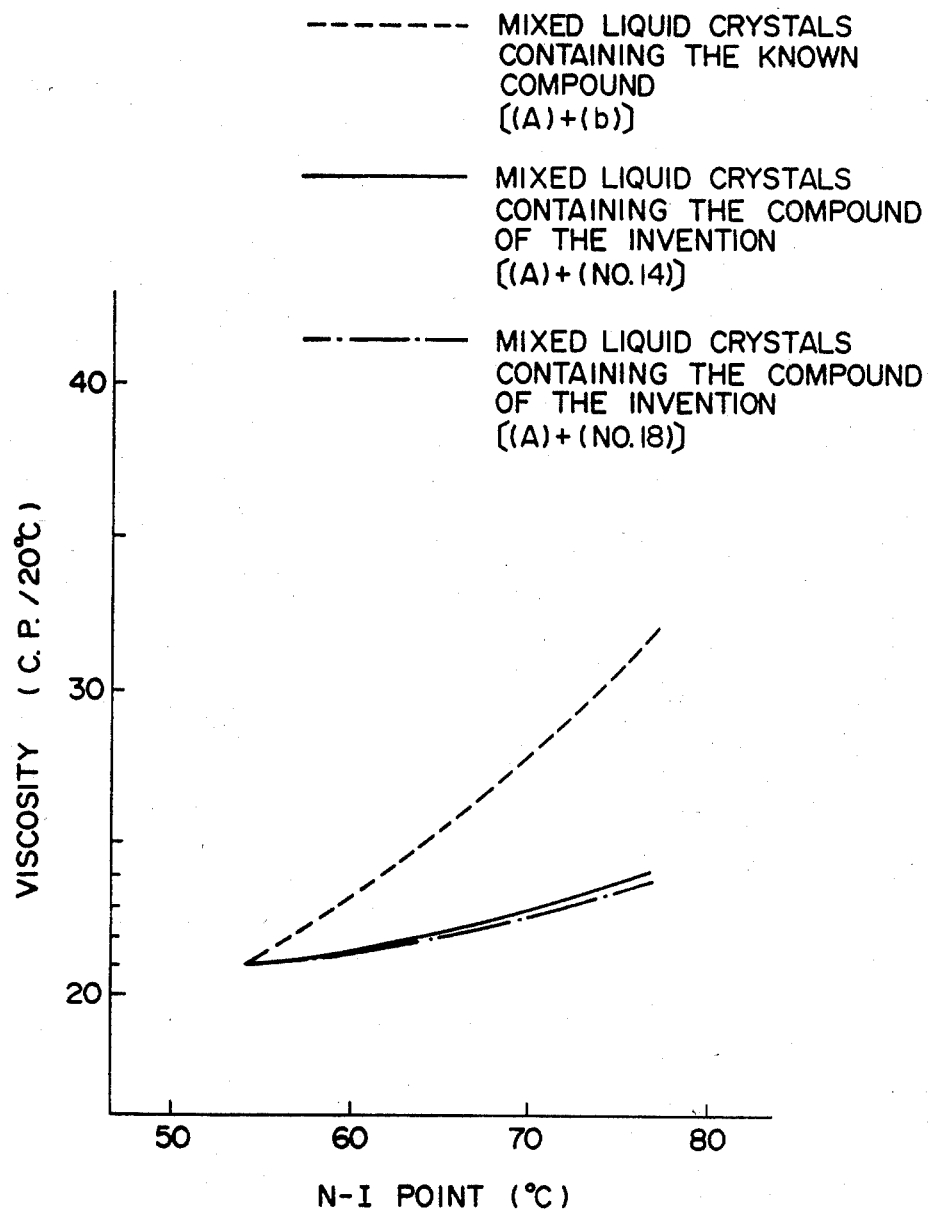

FIGS. 1 and 2 attached hereto are graphs that compare properties of mixed liquid crystals prepared in Comparative Examples 1 and 2.

COMPARATIVE EXAMPLE 1

A known compound of the following formula

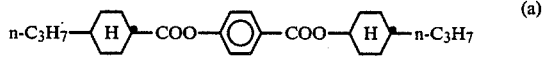
(a)

which has a chemical structure similar to the compound of formula (I) in accordance with this invention and is widely used in order to increase the N-I point of mixed liquid crystals was mixed with the matrix liquid crystals (A) described above in various proportions to provide many mixed liquid crystals having the known compound.

Likewise, one compound of this invention represented by the following formula

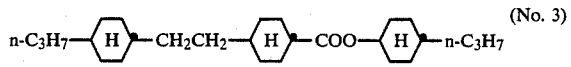
(No. 3)

and another compound of this invention represented by the following formula

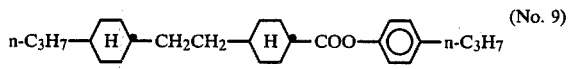
(No. 9)

were mixed respectively in various proportions with the matrix liquid crystals (A) to provide many mixed liquid crystals containing the compounds of this invention.

The N-I points and viscosities were measured for the mixed liquid crystals thus obtained and the resulting data were plotted in FIG. 1.

COMPARATIVE EXAMPLE 2

A known compound of the following formula

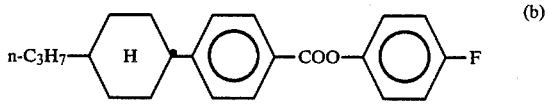
(b)

which has a similar chemical structure to the compound of formula (I) in accordance with this invention and is used in order to increase the N-I point of mixed liquid crystals was mixed in various proportions with the matrix liquid crystals (A) described above to provide many mixed liquid crystals containing the known compound.

Likewise, one compound of this invention represented by the following formula

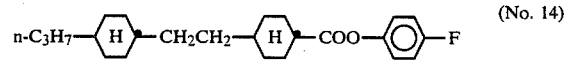
(No. 14)

and another compound of this invention represented by the following formula

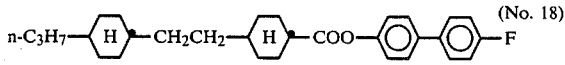
(No. 18)

were mixed respectively in various proportions with the matrix liquid crystals (A) to provide many mixed liquid crystals containing the compounds of this invention.

The N-I points and viscosities were measured for the matrix liquid crystals (A) and mixed liquid crystals thus obtained and the resulting data were plotted in FIG. 2.

EXAMPLE 1

Anhydrous aluminum chloride (16.0 g; 0.120 mole) was added to 100 ml of carbon disulfide, and 7.85 g (0.100 mole) of acetyl chloride was further added at room temperature with stirring. The mixture was cooled to 10° C. With stirring, a solution obtained by dissolving 23.0 g (0.100 mole) of a compound represented by the following formula

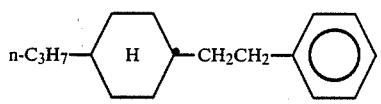

in 50 ml of carbon disulfide was added dropwise, and the reaction was conducted at 10° C. for 5 hours. Thereafter, the temperature was returned to room temperature and the reaction was run for 2 hours. After carbon disulfide was distilled off, the reaction product was added to ice water and stirred at 60° C. for 1 hour. After cooling, the resulting product was extracted with toluene, and the extract was washed with water and dried, followed by distilling off toluene. The residue was recrystallized from ethanol and purified to obtain 22.9 g (0.0842 mole) of a compound represented by the following formula.

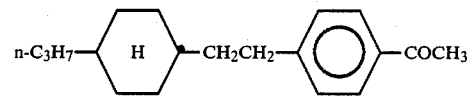

The above compound was dissolved in 230 ml of dioxane and maintained at 30° to 35° C. While stirring the mixture, a solution comprising 150 g of 12% sodium hypochlorite, 13.4 g of sodium hydroxide and 13.7 cc of water was rapidly added dropwise. After the addition, the reaction was performed at 40° to 50° C. for 2 hours, and heating was conducted to 80° C. The reaction product was cooled and acidified with hydrochloric acid. The precipitated crystals were filtered, and the filtrate was washed with water and dried to obtain 18.7 g (0.0682 mole) of a compound represented by the following formula.

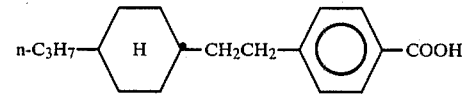

Said compound was dissolved in 300 cc of water along with 3.53 g (0.0750 mole) of sodium hydroxide having a purity of 97%, and 15 g of an Ru-C catalyst (wherein 5% by weight of ruthenium was deposited on the surface of carbon particles having a water content of 70% by weight) was added to the solution, and the mixture was reduced with 3 atm of hydrogen at 80° C. After the reduction was over, the reaction product was filtered and the catalyst was removed. The filtrate was acidified with dilute hydrochloric acid. The precipitate was extracted with ether, and the extract was washed with water and dried, followed by distilling off ether. The residue was heated in a nitrogen stream at 200° C. for 24 hours to transform it thermally. Thereafter, the resulting product was recrystallized from ethanol to obtain 13.5 g (0.0482 mole) of a compound represented by the following formula.

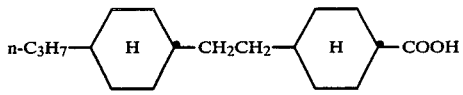

Hundred grams of thionyl chloride was added to said compound and the mixture was refluxed for 3 hours. After thionyl chloride was distilled off, the reaction product was dissolved in 30 cc of toluene.

With stirring at 10° C., the resulting solution was added dropwise to a solution obtained by dissolving 6.84 g (0.0482 mole) of trans-4-propylcyclohexanol and 7.6 g of pyridine in 50 cc of toluene. After the addition, the reaction was conducted at a refluxing temperature for 2 hours. After the reaction, the reaction product was extracted with toluene. The extract was washed with water and dried. Toluene was then distilled off, and the residue was recrystallized from ethanol to afford 14.4 g (0.0356 mole) of a compound represented by the following formula.

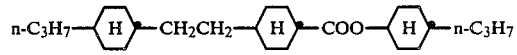

Yield: 35.6%, Transition temperatures: 153° C. (C→N), 166° C. (N⇌I).

EXAMPLE 2

In the same way as in Example 1, a compound of the following formula was obtained.

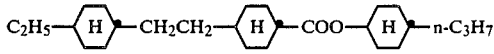

Yield: 32.6%, Transition temperatures: 142° C. (C→N), 155° C. (N⇌I).

EXAMPLE 3

In the same way as in Example 1, a compound of the following formula was obtained.

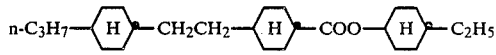

Yield: 33.7%, Transition temperatures: 140° C. (C→N), 151° C. (N⇌I).

EXAMPLE 3

In the same way as in Example 1, a compound of the following formula was obtained.

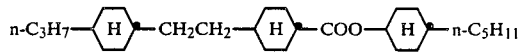

Yield: 34.8%, Transition temperatures: 157° C. (C→N), 169° C. (N⇌I).

EXAMPLE 5

In the same way as in Example 1, a compound of the following formula was obtained.

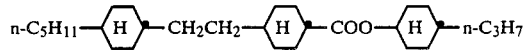

Yield: 34.1%, Transition temperatures: 154° C. (C→N), 167° C. (N⇌I).

EXAMPLE 6

In the same way as in Example 1, a compound of the following formula was obtained.

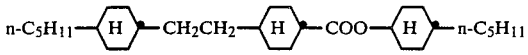

Yield: 35.9%, Transition temperatures: 146° C. (C→S), 155° C. (S⇌N), 161° C. (N⇌I).

EXAMPLE 7

Hundred grams of thionyl chloride was added to 13.5 g (0.0482 mole) of a compound of the following formula obtained in the same way as in Example 1.

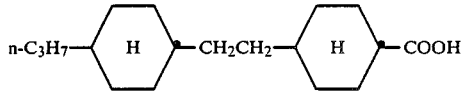

The mixture was refluxed for 3 hours. After thionyl chloride was distilled off, the reaction product was dissolved in 30 cc of toluene.

With stirring at 10° C., the resulting solution was added dropwise to a solution obtained by dissolving 6.56 g (0.0482 mole) of p-propylphenol and 7.6 g of pyridine in 50 cc of toluene. After the addition, the mixture was reacted at a refluxing temperature for 2 hours. After the reaction, the reaction product was extracted with toluene. The extract was washed with water and dried, followed by distilling off toluene. The residue was recrystallized from ethanol to afford 14.6 g (0.0367 mole) of a compound represented by the following formula.

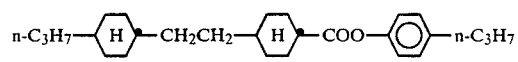

Yield: 36.7%, Transition temperatures: 128° C. (C→S), 131° C. (S⇌N), 165° C. (N⇌I).

EXAMPLE 8

In the same way as in Example 7, a compound of the following formula was obtained.

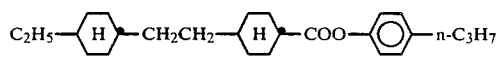

Yield: 34.9%, Transition temperatures: 115° C. (C→N), 152° C. (N⇌I).

EXAMPLE 9

In the same way as in Example 7, a compound of the following formula was obtained.

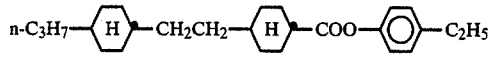

Yield: 35.1%, Transition temperatures: 112° C. (C→N), 149° C. (N⇌I).

EXAMPLE 10

In the same way as in Example 7, a compound of the following formula was obtained.

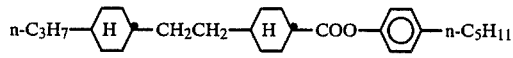

Yield: 37.1%, Transition temperatures: 129° C. (C→S), 135° C. (S⇌N), 167° C. (N⇌I).

EXAMPLE 11

In the same way as in Example 7, a compound of the following formula was obtained.

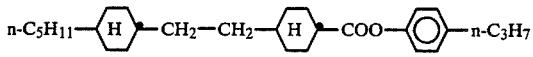

Yield: 36.2%, Transition temperatures: 127° C. (C→S). 134° C. (S⇌N), 166° C. (N⇌I).

EXAMPLE 12

In the same way as in Example 7, a compound of the following formula was obtained.

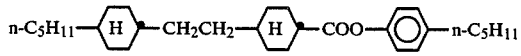

Yield: 37.4%, Transition temperatures: 124° C. (C→S), 147° C. (S⇌N), 163° C. (N⇌I).

EXAMPLE 13

Hundred grams of thionyl chloride was added to 13.5 g (0.0482 mole) of a compound of the following formula obtained in the same way as in Example 1.

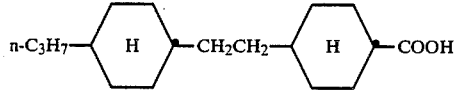

The mixture was refluxed for 3 hours. After thionyl chloride was distilled off, the reaction product was dissolved in 30 cc of anhydrous ether.

With stirring at 10° C., the resulting solution was added dropwise to a solution obtained by dissolving 5.40 g (0.0482 mole) of p-fluorophenol and 7.6 g of pyridine in 50 cc of anhydrous ether. After the addition, the reaction was conducted at a refluxing temperature for 2 hours. After the reaction, the reaction product was extracted with ether. The extract was washed with water and dried, followed by distilling off ether. The residue was recrystallized from ethanol to obtain 13.2 g (0.0353 mole) of a compound represented by the following formula.

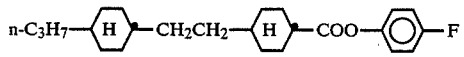

Yield: 35.3%, Transition temperatures: 81° C. (C→N), 156° C. (N⇌I).

EXAMPLE 14

In the same way as in Example 13, a compound of the following formula was obtained.

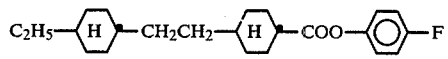

Yield: 33.7%, Transition temperatures: 70° C. (C→N), 136° C. (N⇌I).

EXAMPLE 15

In the same way as in Example 13, a compound of the following formula was obtained.

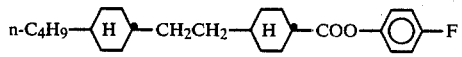

Yield: 34.7%, Transition temperatures: 67° C. (C→N), 148° C. (N⇌I).

EXAMPLE 16

In the same way as in Example 13, a compound of the following formula was obtained.

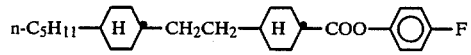

Yield: 37.2%,
Transition temperatures: 83° C. (C→N), 152° C. (N⇌I).

EXAMPLE 17

Hundred grams of thionyl chloride was added to 13.5 g (0.0482 mole) of a compound of the following formula obtained as in Example 1.

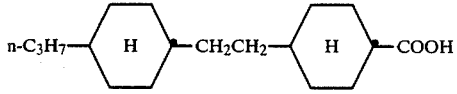

The mixture was refluxed for 3 hours. After thionyl chloride was distilled off, the reaction product was dissolved in 30 cc of toluene.

With stirring at 10° C., the resulting solution was added dropwise to a solution obtained by dissolving 9.06 g (0.0482 mole) of p-fluorophenylphenol and 7.6 g of pyridine in 50 cc of toluene. After the addition, the reaction was performed at a refluxing temperature for 2 hours. After the reaction, the reaction product was extracted with toluene. The extract was washed with water and dried, followed by distilling off toluene. The residue was recrystallized from ethanol to afford 16.1 g (0.0358 mole) of a compound represented by the following formula.

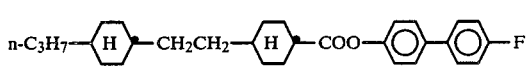

Yield: 35.8%, Transition temperatures: 159° C. (C→N), 260° C. (N⇌I).

EXAMPLE 18

In the same way as in Example 17, a compound of the following formula was obtained.

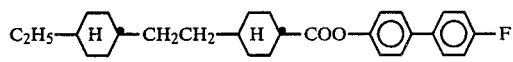

Yield: 32.7%, Transition temperatures: 145° C. (C→N), 248° C. (N⇌I).

EXAMPLE 19

In the same way as in Example 17, a compound of the following formula was obtained.

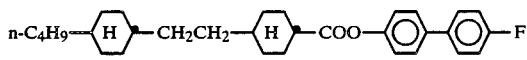

Yield: 33.7%, Transition temperatures: 142° C. (C→N), 251° C. (N⇌I).

EXAMPLE 20

In the same way as in Example 17, a compound of the following formula was obtained.

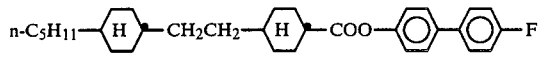

Yield: 34.1%, Transition temperatures: 164° C. (C→N), 258° C. (N⇌I).

We claim:

1. A compound represented by the general formula

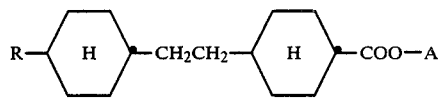

wherein A denotes

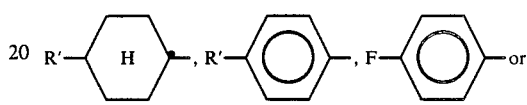

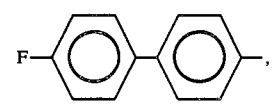

R and R', independently from each other, denote a linear alkyl group having 1 to 9 carbon atoms, and

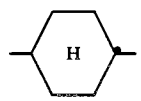

is a cyclohexane ring arranged in a trans(equatorial-equatorial)form.

2. The compound of claim 1 wherein R and R' are selected from the group consisting of $C_2H_5$—, n—$C_3H_7$—, n—$C_4H_9$— and n—$C_5H_{11}$—.

* * * * *